United States Patent
Granger et al.

(10) Patent No.: US 6,280,393 B1
(45) Date of Patent: Aug. 28, 2001

(54) METHOD AND APPARATUS FOR ASSESSING SUSCEPTIBILITY TO STROKE

(75) Inventors: Richard Granger; Gary Lynch, both of Irvine, CA (US)

(73) Assignee: Thuris Corporation, Newport Beach, CA (US)

( * ) Notice: Subject to any disclaimer, the term of this patent is extended or adjusted under 35 U.S.C. 154(b) by 0 days.

(21) Appl. No.: 09/452,202

(22) Filed: Dec. 2, 1999

(51) Int. Cl.$^7$ ........................................... A61B 5/00
(52) U.S. Cl. ............................................ 600/544; 600/547
(58) Field of Search .................................. 600/544–5, 547

(56) References Cited

U.S. PATENT DOCUMENTS

| | | | |
|---|---|---|---|
| Re. 34,015 | * | 8/1992 | Duffy ................................... 600/544 |
| 4,557,270 | | 12/1985 | John . |
| 4,819,648 | * | 4/1989 | Ko ......................................... 600/544 |
| 4,907,597 | | 3/1990 | Chamoun . |
| 5,331,969 | * | 7/1994 | Silberstein ........................... 600/544 |
| 5,365,426 | | 11/1994 | Siegel et al. . |
| 5,671,741 | | 9/1997 | Lang et al. . |

* cited by examiner

Primary Examiner—Robert L. Nasser
(74) Attorney, Agent, or Firm—Sterne Kessler Goldstein & Fox P.L.L.C.

(57) ABSTRACT

A method and apparatus is described herein for assessing the susceptibility of a patient to stroke. The method begins with the step of collecting electrical signals from the brain of the patient under assessment. Signal data corresponding to the collected electrical signals is then compared to at least one standard. In an embodiment of the invention, the standard represents a neural electrical signal taken from a person known to be susceptible to stroke. A positive comparison result suggests susceptibility of the patient under assessment to stroke. Moreover, the comparison result can be used to characterize the pattern of neural blood flow and the degree of susceptibility to stroke. A strong similarity to a standard taken from another patient of known susceptibility suggests that the patient under assessment is experiencing similar neural blood flow and is susceptible to stroke to a similar degree. This information, in turn, can be used to determine both the need for additional testing and/or the appropriate type and extent of therapy. In an alternative embodiment, the standard represents a neural electrical signal taken from the patient under assessment at an earlier point in time. A positive comparison in this case suggests that the condition of the patient under assessment has not changed. A negative comparison result suggests that the neural electrical activity of the patient under assessment has changed, implying possible changes in neural blood flow. This in turn can suggest susceptibility to stroke and the need for additional tests and/or for pharmaceutical or other therapy. The apparatus for collection of electrical signals from the brain includes a headcap with electrodes concentrated in an area corresponding to a particular cranial region of interest.

17 Claims, 3 Drawing Sheets

METHOD AND APPARATUS FOR ASSESSING SUSCEPTIBILITY TO STROKE

BACKGROUND OF THE INVENTION

1. Field of the Invention

The invention described herein relates to medical assessment. In particular, the invention relates to early detection of potential dysfunction.

2. Related Art

Current methods for detecting a patient's susceptibility to stroke are well known, but tend to be costly and/or invasive. Examples include positron emission tomography (PET) and the use of sonogram technology to image capillaries in the brain. At the same time, a considerable amount is known about strokes, and about how and why they occur. It is well known that a stroke can preceded by changes in blood flow in the brain. It is also well known that these changes can occur well in advance of the stroke, sometimes appearing months beforehand. Blood flow may be diminished in a blood vessel, for example, as a result of plaque build-up in the vessel. Moreover, this can lead to the generation of capillaries to compensate for the decreased blood flow in the original blood vessel. Plaque build-up may continue to the point of complete blockage, leading to a stroke. Alternatively, a sudden dislodging of the plaque can bring a sudden increase in blood flow to the newly developed capillaries, which can also lead to a stroke.

While such phenomenon are well understood, the only methods currently available for detection of changes in neural blood flow are costly. Such detection methods are therefore used judiciously; more widespread use would be prohibitively costly. As a result, strokes are not always anticipated. Hence, there is a need for a non-invasive and relatively inexpensive method for detecting a person's susceptibility to stroke.

SUMMARY OF THE INVENTION

The invention described herein is a method and apparatus for assessing the susceptibility of a patient to stroke. The method begins with the step of collecting electrical signals from the brain of the patient under assessment. Signal data corresponding to the collected electrical signals is then compared to at least one standard. In an embodiment of the invention, the standard represents a neural electrical signal taken from a person known to be susceptible to stroke. A positive comparison result suggests susceptibility of the patient under assessment to stroke. Moreover, the comparison result can be used to characterize the pattern of neural blood flow and the degree of susceptibility to stroke. A strong similarity to a standard taken from another patient of known susceptibility suggests that the patient under assessment is experiencing similar neural blood flow and is susceptible to stroke to a similar degree. This information, in turn, can be used to determine both the need for additional testing and/or the appropriate type and extent of therapy. In an alternative embodiment, the standard represents a neural electrical signal taken from the patient under assessment at an earlier point in time. A positive comparison in this case suggests that the condition of the patient under assessment has not changed. A negative comparison result suggests that the neural electrical activity of the patient under assessment has changed, implying possible changes in neural blood flow. This in turn can suggest susceptibility to stroke and the need for additional tests and/or for pharmaceutical or other therapy. The apparatus for collection of electrical signals from the brain includes a headcap with electrodes concentrated in an area corresponding to a particular cranial region of interest.

BRIEF DESCRIPTION OF THE FIGURES

The foregoing and other features and advantages of the invention will be apparent from the following, more particular description of a preferred embodiment of the invention, as illustrated in the accompanying drawings.

DETAILED DESCRIPTION OF THE PREFERRED EMBODIMENTS

A preferred embodiment of the present invention is now described with reference to the figures where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other devices and applications.

I. Overview

The invention provides a method of identifying persons who may be susceptible to stroke and who may therefore require additional testing and/or pharmaceutical or other therapy. The extent of a person's susceptibility and the pattern of the person's neural blood flow can also be characterized. Stroke is typically preceded by irregularities in blood flow in the brain. These irregularities reveal themselves through changes in neural electrical activity. The invention detects changes in neural electrical activity of a patient, which allows inferences to be made as to a patient's possible susceptibility to stroke.

The method of the invention begins with the step of collecting electrical signals from the brain of a patient under assessment. The collected electrical signals can then be compared to standards. For example, the collected electrical signals can be compared to signals taken from one or more persons known to be susceptible to stroke. Alternatively, the collected electrical signals of a patient under assessment can be compared to signals that were taken at one or more earlier points in time from the same patient. The latter approach allows a patient to be monitored over time to see whether the neural electrical activity has changed. Significant change could indicate a change in vascular condition of the patient, which could, in turn, suggest susceptibility to stroke.

II. Process

The process of the invention includes the collection of electrical signals from the brain of a patient under assessment. The signals can then be compared to signals of persons known to be susceptible to stroke. The signals can alternatively be compared to signals taken from the same patient at earlier points in time, in order to monitor changes in the neurological health of the patient over time. In alternative embodiments, the collected electrical signals can be processed prior to any comparison, yielding signal data, a form of the collected electrical signals that facilitates comparison.

A. Use of Raw Electrical Signals Collected from a Patient

Figure 1:
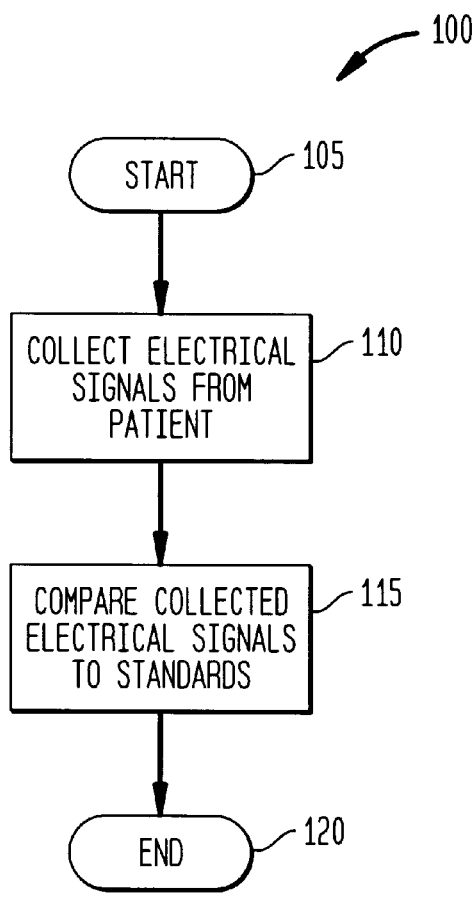
FIG. 1 is a flowchart illustrating operation of an embodiment of the invention in a group testing environment, where unprocessed collected electrical signals are compared to one or more standards.

An embodiment of the invention is illustrated in flowchart 100 of FIG. 1. The process begins with a step 105. In a step 110, electrical signals are collected from the brain of a patient under assessment. This can be done using a conventional electroencephalograph (EEG) apparatus and method, in which case the collected electrical signals represent one or more free running EEGs captured at various points on the surface of the brain. Alternatively, the electrical signals can be collected through an evoked response potential (ERP) apparatus and method. Here, electrical signals are captured at a plurality of points on the surface of the brain immediately after the patient under assessment has been exposed to a sensory stimulus, such as a flash of light, an auditory tone, or a tactile stimulus. An apparatus for capturing neural electrical signals is discussed in greater detail in section III below. In general, the use of EEGs and ERPs to capture neural electrical activity is well known to those skilled in the relevant art. In either case, the result of step 110 is a set of signals or graphs, where each graph represents electrical activity, over time, at a point on the brain surface.

In a step 115, the collected electrical signals of the patient under assessment are compared to other signals that represent standards for comparison. In an embodiment of the invention, the signals of the patient under assessment are compared to signals taken from one or more persons known to be susceptible to stroke.

Persons known to be susceptible to stroke can be identified as such by using traditional longitudinal studies. The neural electrical activity of each person in a group of test patients is first benchmarked. The group is then tracked over time, and those who eventually suffer a stroke are identified. The benchmarked neural signals of those test patients who later suffered a stroke are then used as standards for comparison for the patient under assessment. Similarity between the collected electrical signals and the neural signals of persons who later suffered a stroke can indicate that the patient under assessment is likewise susceptible.

The comparison step 115 can be performed in any of several ways that are well known to those skilled in the relevant art. Comparison may be done by statistical processing, for example, or by image analysis. A positive comparison result raises the possibility that the patient under assessment is susceptible to stroke and should be tested further and/or treated using pharmaceutical or other means. In particular, the comparison result can be used to determine the degree of susceptibility to stroke and to characterize the pattern of neural blood flow of the patient under assessment. In assessing the susceptibility of a patient to acute medial cerebral cortical infarction, for example, susceptibility can coincide with a state of hypoperfusion. Hypoperfusion refers to a condition wherein the volume of blood flowing through different neural blood vessels has changed. Step 115 can determine similarity between the state of hypoperfusion of the patient under assessment and the state of hypoperfusion indicated by the standard.

A strong similarity to a standard taken from another patient of known susceptibility suggests that the patient under assessment is susceptible to a similar degree, and is experiencing a similar pattern of neural blood flow, e.g., a similar state of hypoperfusion. This information, in turn, can be used to determine the both the need for additional testing and/or the appropriate type and extent of therapy.

Figure 2:
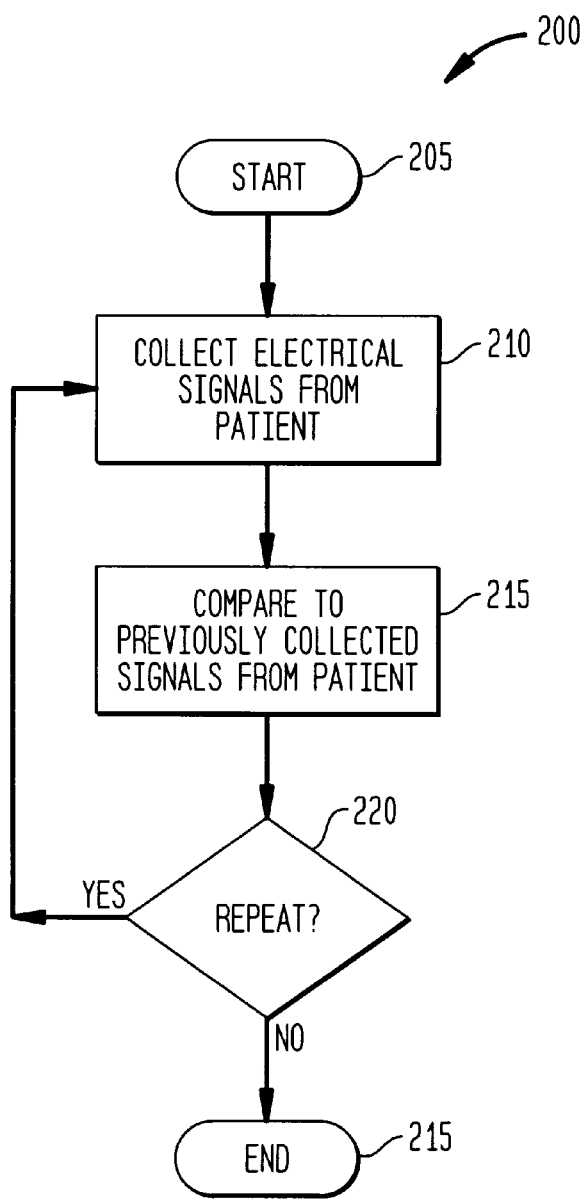
FIG. 2 is a flowchart illustrating operation of an embodiment of the invention where unprocessed electrical signals collected from a patient are compared to signals collected earlier from the patient.

In an alternative embodiment, the signals of the patient under assessment are compared to signals collected from the same patient at one or more earlier points in time. This allows the detection of significant changes in the neural electrical activity of the patient under assessment. This is illustrated in flowchart 200 of FIG. 2. The process starts with a step 205. In a step 210, electrical signals are collected from the brain of the patient under assessment, as in the case of process 100. In a step 215, the collected electrical signals are compared to signals collected previously from the same patient. In this way, any significant changes in the neural electrical activity of the patient can be revealed. As in the case of process 100, comparison can be performed using methods such as statistical processing or image analysis. A negative comparison result suggests that the condition of the patient under assessment has changed, and that the patient may be susceptible to stroke and should be tested further and/or treated using pharmaceutical or other therapy.

In a step 220, a determination is made as to whether additional signals are to be collected from the patient at some later point, e.g., one month hence. If so, the process continues at that time with step 210. Process 200 therefore allows monitoring over time, so that a patient can be checked and rechecked for changes that can indicate irregularities in neural blood flow and possible susceptibility to stroke.

B. Use of Signal Data Derived from Collected Electrical Signals

Figure 3:
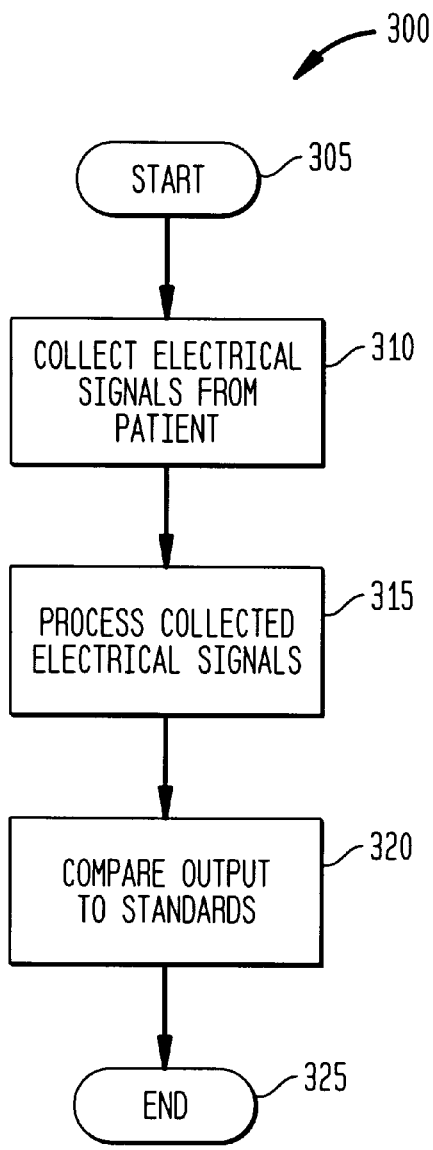
FIG. 3 is a flowchart illustrating operation of an embodiment of the invention in a group testing environment, where processed collected electrical signals are compared to one or more standards.

In an alternative embodiment of the invention, the signals collected from the patient under analysis are processed prior to comparison with other signals. This processing, described below, results in signal data that is a function of the collected electrical signals. Signal data facilitates the subsequent comparison step. Such an embodiment is illustrated as flowchart 300 of FIG. 3. The process begins with a step 305. In a step 310, electrical signals are collected from the brain of the patient under assessment. As described above, signal collection can be performed using an EEG procedure, an ERP procedure, or a similar method. In a step 315, the collected electrical signals are processed. The collected electrical signals can, for example, undergo a noise reduction process. The collected electrical signals can also be projected into an information subspace of lower dimensionality. In this process, each collected electrical signal is first sampled in the time domain to form an ordered set, or vector, of numerical values. The construction of a vector from an analog signal is known herein as vectorization. Some components of the vector are then deleted to form a vector of lower dimension, known as a projection. The deletion of components can be done either randomly or deterministically. The projections can then be compared to vectorized versions of one or more standard signals in a subsequent comparison step. The process of projecting collected electrical signals into an information subspace of lower dimensionality is described in greater detail in U.S. patent application Ser. No. 09/407,368, incorporated herein in its entirety.

Processing of collected electrical signals can also include the extraction of features of the signals. The overall power of a collected electrical signal is an example of a feature that can be extracted. Another example of an extractable feature is the degree of symmetry between the power in signals collected from the left and right hemispheres of the brain. Other features of a signal can be extracted, as is well known in the art. Extracted features can then be compared to analogous features of one or more standard signals in a subsequent comparison step. The procedures of noise reduction, projection, and feature extraction are presented merely as examples of the processes that can be used in step 315, and are not meant to limit the scope of the invention. Moreover, the example processes described here can also be combined in step 315. Noise reduction, for example, can be performed prior to projection or feature extraction.

In a step 320, the signal data is compared to standard signals. In a manner analogous to step 115, in an embodiment of the invention, the signal data of the patient under assessment is compared to signals taken from one or more persons known to be susceptible to stroke. If the signal data represents projections of the electrical signals originally collected from the patient under assessment, the projections are compared to vectorized versions of the standard signals. If the signal data represents features extracted from the collected signals, these features are compared to analogous features taken from the standard signals. If the signal data is a reduced noise version of the originally collected signals, then this noise-reduced version is compared to the standard signals. In any event, as in the case of process 100, a positive comparison result suggests the possibility that the patient under assessment is susceptible to stroke and should be tested further and/or treated using pharmaceutical or other means. In particular, the comparison result can be used to determine the degree of susceptibility to stroke, and to characterize the pattern of neural blood flow, e.g., the state of hypoperfusion of the patient under assessment. A strong similarity to a standard signal taken from another patient of known susceptibility implies that the patient under assessment is susceptible to a similar degree, and is experiencing a similar pattern of neural blood flow. This information, in turn, can be used to determine the both the need for additional testing and/or the appropriate type and extent of therapy.

Figure 4:
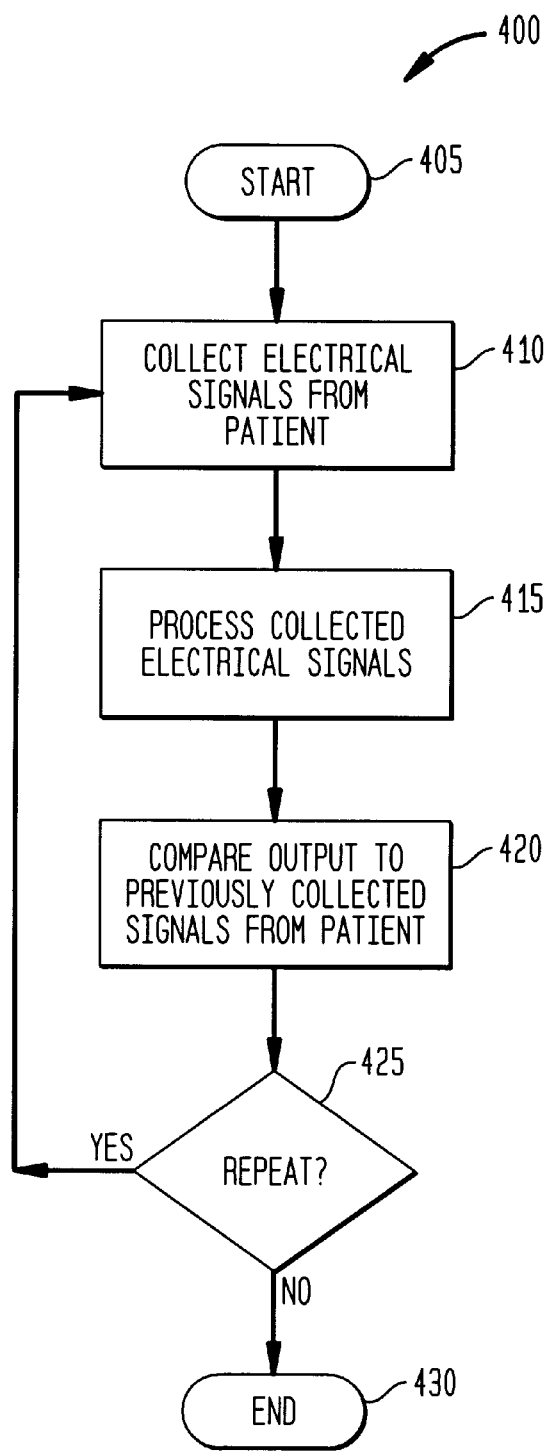
FIG. 4 is a flowchart illustrating operation of an embodiment of the invention where electrical signals are collected from a patient and processed, then compared to signal data derived earlier from the patient.

An alternative embodiment is illustrated by flowchart 400 of FIG. 4. Here, signal data of the patient under assessment is compared to signals previously collected from the same patient. The process begins with a step 405. In a step 410, electrical signals are collected from the brain of the patient under assessment. In a step 415, the collected electrical signals are processed. As described above with respect to step 315, processing can take the form of noise reduction, projection, or feature extraction, so as to yield signal data. Step 415 may alternatively include other forms of processing in other embodiments of the invention, wherein the processing facilitates a subsequent comparison step 420. In step 420, signal data is compared to neural electrical signals collected from the patient at one or more points in the past. If the signal data represents projections of the signals originally collected from the patient under assessment, the projections are compared to vectorized versions of the signals collected previously from the same patient. If the signal data represents features extracted from the collected electrical signals, these features are compared to analogous features taken from the previously collected signals. If the signal data is a reduced noise version of the originally collected electrical signals, then this noise-reduced version is compared to the previously collected signals. In any event, as in the case of process 200, a negative comparison result suggests that the patient under assessment may be susceptible to stroke and should be tested further.

III. Signal Collection Apparatus

As discussed above, apparatus for the collection of neural electrical signals is well known to persons skilled in the relevant art. The collection of such signals can be improved, for purposes of the above method, by modifying the conventional collection apparatus. Since the method described in section II collects signals related to blood flow in the brain, collection can be concentrated in those regions of the brain surface corresponding to blood vessels of interest.

Such a modified apparatus can consist of a conventional headcap as used in the collection of EEG or ERP signals, with additional electrodes placed in proximity to regions of the brain surface fed by a blood vessel of interest, such as the medial cerebral artery. This permits the collection of increased amounts of information from the regions of interest, improving the reliability of the process of section II.

Figure 5A:
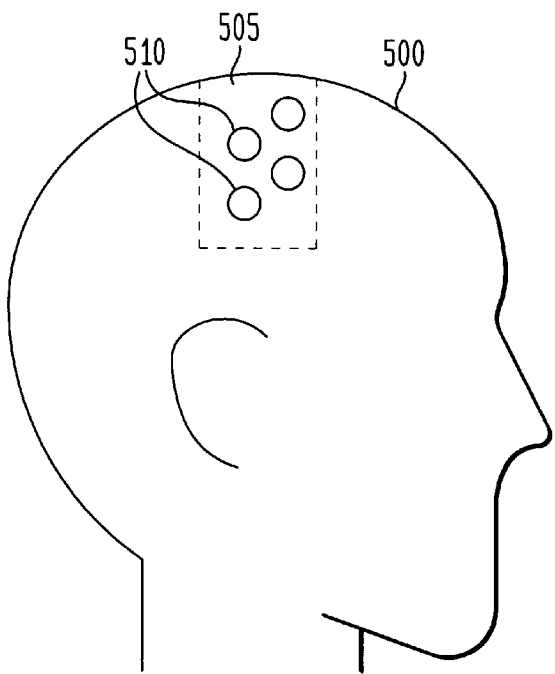
FIGS. 5A and 5B illustrate a headcap that can be used in the collection of electrical signals from the brain of a patient under assessment.
Figure 5B:
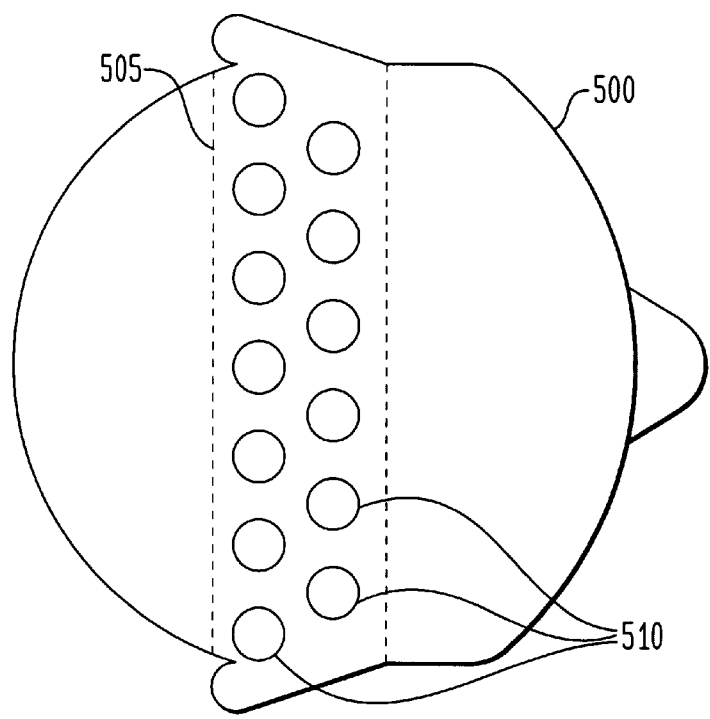

An exemplary headcap apparatus, according to an embodiment of the invention, is illustrated in FIGS. 5A and 5B. These figures represent side and top views, respectively, of a headcap 505 as worn by a patient 500. In the embodiment illustrated, the headcap 505 covers the region of the brain surface that is fed by the medial cerebral artery. Other embodiments of the headcap can concentrate electrodes on other regions of the brain surface, such as the region associated with the somatosensory motor cortex. Headcap 505 includes electrodes 510. While FIG. 5B shows 13 electrodes 510, other embodiments can have a different number. In alternative embodiments, the headcap can cover the skull more completely. Moreover, such a headcap can include electrodes thoughout, while concentrating electrodes in a region of interest.

Note that while an apparatus having an increased number of electrodes improves the collection of information, it is not essential to the method of section II. The method described above can be performed with a conventional, unmodified headcap as used in the collection of EEG or ERP signals.

IV. Conclusion

While various embodiments of the present invention have been described above, it should be understood that they have been presented by way of example, and not limitation. It will be apparent to persons skilled in the relevant art that various changes in detail can be made therein without departing from the spirit and scope of the invention. Thus the present invention should not be limited by any of the above-described exemplary embodiments, but should be defined only in accordance with the following claims and their equivalents.

What is claimed is:

1. A method of determining the susceptibility to suffering a stroke of a patient under assessment, the method comprising the steps of:

(a) collecting electrical signals from the brain of the patient under assessment before the patient under assessment suffers the stroke;

(b) comparing signal data corresponding to the collected electrical signals to at least one standard to produce comparison results, wherein the signal data is derived from the collected electrical signals; and (c) interpreting the comparison results.

2. The method of claim 1, wherein said step (a) comprises the step of collecting at least one electroencephalograph (EEG).

3. The method of claim 1, wherein said step (a) comprises the steps of:

(i) performing at least one evoked response potential (ERP) trial on the patient under assessment; and (ii) capturing the electrical signals that result from the at least one ERP trial.

4. The method of claim 1, further comprising the step of:
(d) processing the collected electrical signals to derive signal data for subsequent comparison to the at least one standard; performed after step (a) and before step (b).

5. The method of claim 4, wherein said step (d) comprises the step of performing noise reduction on the collected electrical signals.

6. The method of claim 4, wherein said step (d) comprises the step of performing feature extraction on the collected electrical signals.

7. The method of claim 4, wherein said step (d) comprises the step of generating a plurality of projections of the collected electrical signals.

8. The method of claim 1, wherein said step (b) comprises the step of comparing the signal data corresponding to the collected electrical signals to at least one standard, wherein the at least one standard comprises signal data from a patient known to be susceptible to stroke.

9. The method of claim 1, wherein said step (b) comprises the step of comparing signal data corresponding to the collected electrical signals to at least one standard, wherein the at least one standard comprises signal data derived from electrical signals that were collected at an earlier time from the patient under assessment.

10. The method of claim 1, wherein said step (b) comprises the step of comparing signal data corresponding to the collected electrical signals to at least one standard using statistical processing.

11. The method of claim 1, wherein said step (b) comprises the step of comparing signal data corresponding to the collected electrical signals to at least one standard using image analysis.

12. The method of claim 1, wherein said step (c) comprises the step of determining whether the patient under assessment is susceptible to suffering a stroke.

13. The method of claim 1, wherein said step (c) comprises the step of determining a degree of susceptibility of the patient under assessment to suffering a stroke.

14. The method of claim 1, wherein said step (c) comprises the step of characterizing a pattern of neural blood flow in the patient under assessment.

15. The method of claim 1, wherein said step a) comprises collecting electrical signals from the surface of the brain of the patient under assessment, using a headcap that comprises a plurality of electrodes concentrated in at least one region of said headcap, wherein the plurality of electrodes of the at least one region of the headcap are in electrical contact with at least one region of the surface of the brain.

16. The method of claim 15, wherein the at least one region of the surface of the brain comprises a region supplied with blood by the medial cerebral artery.

17. The method of claim 15, wherein the at least one region of the surface of the brain comprises the somatosensory cortex.

* * * * *

UNITED STATES PATENT AND TRADEMARK OFFICE
CERTIFICATE OF CORRECTION

PATENT NO. : 6,280,393 B1  
DATED : August 28, 2001  
INVENTOR(S) : Granger et al.

It is certified that error appears in the above-identified patent and that said Letters Patent is hereby corrected as shown below:

<u>Column 1,</u>
Line 3, after the title of the invention and before the heading "BACKGROUND OF THE INVENTION" please insert the heading and paragraph as follows:
-- STATEMENT AS TO RIGHTS TO INVENTIONS MADE UNDER FEDERALLY-SPONSORED RESEARCH AND DEVELOPMENT. This invention was made with Government support under N00014-97-C-0192 awarded by the Office of Naval Research. The U.S. Government has certain rights in this invention. --.

Signed and Sealed this

Twenty-first Day of January, 2003

JAMES E. ROGAN
*Director of the United States Patent and Trademark Office*